United States Patent [19]

Eichler et al.

[11] Patent Number: 4,935,561

[45] Date of Patent: Jun. 19, 1990

[54] PROCESS FOR ISOMERIZING MONOCHLOROTOLUENES OR DICHLOROTOLUENES

[75] Inventors: Klaus Eichler, Eschborn; Hans-Jürgen Arpe; Herbert Baltes, both of Frankfurt am Main; Ernst I. Leupold, Neu-Anspach, all of Fed. Rep. of Germany

[73] Assignee: Hoechst Aktiengesellschaft, Frankfort am Main, Fed. Rep. of Germany

[21] Appl. No.: 740,180

[22] Filed: May 31, 1985

[30] Foreign Application Priority Data

Jun. 2, 1984 [DE] Fed. Rep. of Germany ....... 3420706
Sep. 13, 1984 [DE] Fed. Rep. of Germany ....... 3433812

[51] Int. Cl.$^5$ ...................... C07C 17/24; C07C 17/00
[52] U.S. Cl. .................................................. 570/202
[58] Field of Search ......................................... 570/202

[56] References Cited

U.S. PATENT DOCUMENTS

| | | | |
|---|---|---|---|
| 4,175,175 | 11/1979 | Johnson et al. | 528/125 |
| 4,368,339 | 1/1983 | Tada et al. | 570/202 |

FOREIGN PATENT DOCUMENTS

| | | | |
|---|---|---|---|
| 111362 | 9/1979 | European Pat. Off. . | |
| 42225 | 5/1981 | European Pat. Off. . | |
| 046665 | 8/1981 | European Pat. Off. . | |
| 51741 | 10/1981 | European Pat. Off. . | |
| 46665 | 3/1982 | European Pat. Off. | 570/202 |
| 062261 | 3/1982 | European Pat. Off. . | |
| 171008 | 6/1982 | European Pat. Off. . | |
| 62261 | 10/1982 | European Pat. Off. | 570/202 |
| 077523 | 10/1982 | European Pat. Off. . | |
| 72008 | 2/1983 | European Pat. Off. | 570/202 |
| 85377 | 8/1983 | European Pat. Off. . | |
| 143407 | 6/1985 | European Pat. Off. . | |
| 2212810 | 3/1971 | Fed. Rep. of Germany . | |
| 144330 | 8/1983 | Japan | 570/202 |
| 1334243 | 9/1970 | United Kingdom . | |
| 2023562 | 6/1979 | United Kingdom . | |

OTHER PUBLICATIONS

"Ullmann's Encyclopedia of Industrial Chemistry", (1975), 4th Edition, vol. 9, pp. 512–513.
G. A. Ohah, M. W. Meyer, J. Org. Chem., 27, 3464, (1964).
"Methods of Organic Chemistry", vol. V/3, (1962), pp. 659 and 660.
Chemical Abstracts, 100, 51,224 s.

*Primary Examiner*—Werren B. Lone
*Attorney, Agent, or Firm*—Curtis, Morris & Safford

[57] ABSTRACT

The invention relates to a process for isomerizing monochlorotoluenes or dichlorotoluenes on a zirconium-containing zeolite catalyst of the Pentasil type. Catalysts of this type are distinguished by a particularly high activity coupled with a long service life. In particular, the invention relates to the preparation of a mixture 3-chlorotoluene and 4-chlorotoluene by isomerizing 2-chlorotoluene on zircoium-containing zeolite catalysts of the Pentasil type.

The invention also relates to the preparation of a mixture of 2,5-dichlorotoluene and 3,4-dichlorotoluene by appropriate isomerization of 2,4-dichlorotoluene, and to the preparation of a mixture of 2,4-dichlorotoluene and 2,5-dichlorotoluene by appropriate isomerization of 3,4-dichlorotoluene.

10 Claims, No Drawings

PROCESS FOR ISOMERIZING MONOCHLOROTOLUENES OR DICHLOROTOLUENES

The present invention relates to a process for isomerizing monochlorotoluenes or dichlorotoluenes.

When toluene is chlorinated in the presence of catalysts the isomeric, nuclear-chlorinated 2-, 3- and 4-chlorotoluenes are formed in a ratio which varies depending on the type of catalyst employed and on the reaction conditions chosen. Thus the chlorination of toluene, for example at 50° C. in the presence of $FeCl_3$ as catalyst, results in a product mixture composed of 19% by weight of toluene, 49% by weight of 2-chlorotoluene, 2% by weight of 3-chlorotoluene and 25.5% by weight of 4-chlorotoluene. In addition, 4.5% of dichlorotoluene are also formed (Ullmanns Encycl. der techn. Chemie ["Ullmann's Encyclopedia of Industrial Chemistry"] (1975) volume 9, page 512). The use of $TiCl_4$, $SnCl_4$, $WCl_6$ or $ZrCl_4$ as catalysts at a chlorination temperature of 10°-30° C. raises the proportion of 2-chlorotoluene to 75% by weight (U.S. Pat. No. 3,000,975), while the use of disulfur dichloride and the metal chlorides mentioned or the use of sulfur and $SbCl_3$ shifts the ratio of isomers in favor of 4-chlorotoluene (U.S. Pat. No. 1,946,040). In no case is it possible to obtain a single-substance isomer by means of a suitable choice of the catalyst or of the reaction conditions. In particular, pure 3-chlorotoluene cannot be prepared by direct chlorination of toluene.

It is already known that chlorotoluenes can be isomerized in the presence of $AlCl_3$ (G. A. Olah, M. W. Meyer, J. Org. Chem. 27, 3464 (1964)) or of $HF/BF_3$ (U.S. Pat. No. 3,742,073). However, considerable amounts of catalyst are required for this, and corrosion problems are encountered. The isomerization of chlorotoluenes on zeolite catalysts has also already been described (European Patent No. A1-46,665 and European Patent A1-72008). A factor of disadvantageous effect here is the rapid deactivation of the zeolite catalysts by coking, which results in a rapid decline in the conversion after a short time. Although a process in which this deactivation manifests itself to a substantially smaller extent is described in European Patent No. A1-62,261, it is then necessary to add an organic diluent, which makes it very expensive to carry out the isomerization on an industrial scale, since this diluent has to be separated off and recycled to the process.

In general, dichlorotoluenes are also prepared industrially by chlorinating toluene in the nucleus. In this reaction, a mixture of 2-chlorotoluene and 4-chlorotoluene is formed first, and the further chlorination of this results in 2,4-dichlorotoluene and - to a lower extent - 2,3-dichlorotoluene (R. Stroh in: Houben-Weyl, Methoden der Organischen Chemie ["Methods of Organic Chemistry"], volume V/3, halogen compounds, Stuttgart 1962, pages 659 and 660).

The other isomers of dichlorotoluene are formed only to a small extent or not at all when toluene is chlorinated (Ullmanns Enzyklopädie der Technischen Chemie U ["Ullmann's Encyclopedia of Industrial Chemistry"], 4th edition, volume 9, page 513). In some cases their preparation requires involved and expensive multi-stage syntheses. Thus, for example, 2,5-dichlorotoluene can be obtained by diazotization using Sandmeyer's method from 5-chloro-2-aminotoluene or from 2,5-diaminotoluene.

It is already known that dichlorotoluenes can be isomerized on zeolite catalysts (Chemical Abstracts 100, 51,224 s). A factor of disadvantageous effect here is the rapid deactivation of the zeolite catalysts by coking, which results in a rapid decline in the conversion after a short time.

It was therefore required to develop a process for isomerizing monochlorotoluenes or dichlorotoluenes in which the catalyst displays a long service life, a low deactivation and a high activity, without the addition of an organic diluent.

It has now been found that, when monochlorotoluouenes and dichlorotoluenes are isomerized on zirconium-containing zeolites of the Pentasil type, such as are described, for example, in European Patent No. A2-77,523 higher yields and longer service lives can be obtained than with the catalysts hitherto described, without the need to add an organic diluent.

The invention relates, therefore, to a process for isomerizing one or more monochlorotoluenes or one or more dichlorotoluenes on a zeolite catalyst, which comprises using a zirconium-containing zeolite of the Pentasil type. The present invention relates especially to a process for the preparation of a mixture of 3-chlorotoluene and 4-chlorotoluene by isomerizing 2-chlorotoluene on a zeolite of this type. The present invention also relates to a process for isomerizing 2,4-dichlorotoluene or 3,4-dichlorotoluene on a zeolite catalyst of this type.

On the basis of the state of the art it was surprising and in no way forseeable that higher isomerization yields coupled with a lower deactivation of the catalyst could be achieved on zirconium-containing zeolites of the Pentasil type than when using the zirconium-free zeolite described above. A comparison between Example 1 and comparison Example 1, and between Example 2 and comparison Example 2 shows that considerably higher isomerization yields are obtained under identical conditions using the catalysts according to the invention. In addition, no change in the catalytic activity is observed in Example 1 over a period of 90 hours, whereas a marked reduction in the activity as a result of deactivation of the catalyst takes place within a much shorter period using the catalysts hitherto known, as is also shown by the comparison example. In addition, the catalyst according to the invention has a more selective action, since the formation of by-products is less.

Examples 3 and 4 shows that the partly deactivated catalyst regains full activity after regeneration. When 2,4-dichlorotoluene is isomerized, 2,5-dichlorotoluene and 3,4-dichlorotoluene are mainly formed, while the isomerization of 3,4-dichlorotoluene results in 2,4-dichlorotoluene and 2,5-dichlorotoluene. It is therefore possible to prepare 2,5-dichlorotoluene from 2,4-dichlorotoluene, if unreacted 2,4-dichlorotoluene and the 3,4-dichlorotoluene formed are recycled to the reactor.

For the isomerization according to the invention of monochlorotoluene, 2-, 3- or 4-chlorotoluene or a mixture composed of two or all three of these isomers is brought into contact with a zirconium-containing zeolite catalyst of the Pentasil type. If a mixture containing all three isomers is employed, it is, of course, only possible to observe isomerization if the composition of the starting mixture at the reaction temperature differs from that of a chlorotoluene mixture which is present in the thermodynamic equilibrium.

For the isomerization according to the invention of dichlorotoluene, a dichlorotoluene or a mixture of several isomeric dichlorotoluenes, either on their own or together with one or more organic diluents, is passed, in gas or liquid form over the zeolite catalyst. The dichlorotoluene generally employed is 2,4-dichlorotoluene, which is available on a large industrial scale. However, the other isomeric dichlorotoluenes, for example 3,4-dichlorotoluene or 2,6-dichlorotoluene, can also be isomerized by the process according to the invention. Again, it is, of course, only possible to observe isomerization, if the composition of the starting mixture differs from that of a mixture which is present in the thermodynamic equilibrium. Suitable organic diluents are, in particular, aromatic hydrocarbons, preferably chlorobenzene, benzene and/or toluene. The molar ratio of the diluent to dichlorotoluene is generally 0:1 to 10:1, preferably 0:1 to 3:1.

Catalysts suitable for the isomerization of monochlorotoluenes and dichlorotoluenes are zirconium silicates and zirconium aluminosilicates having a Pentasil structure.

In this respect, the definition of Kokotailo and Meier ("The Pentasil family of high silicon crystalline materials" in Special Publication No. 33 of the Chemical Society, London, 1980) applies to the term Pentasils. The Pentasil family embraces, for example, the synthetic zeolites ZSM-5 (U.S. Pat. No. 3,702,886), ZSM-8 (British Patent No. 1,334,243), ZSM-11 (U.S. Pat. No. 3,709,979) and ZSM-23 (U.S. Pat. No. 4,076,842).

Zirconosilicates and zirconoaluminosilicates suitable in the process according to the invention are those having the ZSM-5 structure, preferably those having the following composition, expressed in molar ratios of the oxides:

$SiO_2$: (0–0.15) $Al_2O_3$: (0.002–1.0) $ZrO_2$, especially
$SiO_2$: (0–0.1) $Al_2O_3$: (0.01–0.4) $ZrO_2$ (see European Patent A2-77,523).

These zirconium-containing zeolites can be prepared by the same methods and using the same organic compounds as have also been described for the synthesis of the zirconium-free zeolite ZSM-5, for example using the following:

alkylammonium compounds (U.S. Pat. No. 3,702,886)
alkylamines (U.S. Pat. No. 4,151,189)
alkyldiamines (German Offenlegungsschrift No. 2,817,576 and German Offenlegungsschrift No. 2,831,334)
alkylamines in the presence of alkylating agents (European Laid-open Specification No. 11,362 and German Auslegeschrift No. 2,212,810)
aminoalcohols (British Patent No. 2,023,562)
alcohols (German Offenlegungsschrift No. 2,935,123, U.S. Pat. No. 4,175,114, European Laid-open Specification 42,225 and German Offenlegungsschrift 2,643,929) and
ethers (European Laid-open Specification 51,741).

It is preferable to use alkylammonium compounds, alkyldiamines, or alkylamines in the presence of alkylating agents. Amongst the alkylammonium compounds, the tetrapropylammonium compounds are particularly preferred, for example the hydroxide or one of the halides. A particularly suitable alkyldiamine is hexamethylenediamine.

The zirconium-containing Pentasils are synthesized by mixing one or more compounds from the classes mentioned with zirconium compounds and with silicon compounds and sodium compounds and water - and, in the case of aluminosilicate, additionally with aluminum compounds and heating this mixture in a closed vessel.

In addition, seed crystals of a Pentasil are preferably added to the mixture before it is heated.

If tetrapropylammonium compounds are used, the starting compounds are generally employed in the folowing ratio, expressed in molar ratios of the oxides:
$SiO_2$: (0–0.2) $Al_2O_3$: (0.01–1.0) $ZrO_2$: (0.01–0.5)
$Na_2O$: (0.02–1.0) $R_2O$: (5–100) $H_2O$,
preferably in the ratio
$SiO_2$:(0–0.1) $Al_2O_3$:(0.01–0.4) $ZrO_2$: (0.02–0.3)
$Na_2O$: (0.03–0.6) $R_2O$: (10–40) $H_2O$,
wherein R is tetrapropylammonium.

The following are examples of silicon, aluminum, zirconium and sodium compounds which can be employed: silica gel, sodium silicate, aluminum hydroxide, aluminum sulfate, sodium aluminate, aluminum halides, aluminum metahydroxide, zirconium halides, zirconium sulfate, zirconyl chloride, sodium hydroxide, sodium sulfate and sodium halides. Other compounds of the five elements mentioned are, however, also suitable for the preparation of the zeolites.

The mixture of the particular compounds selected and water is generally heated in a closed vessel for 18 to 360 hours, preferably 24 to 240 hours, at a temperature between 100° and 200° C., preferably between 130° and 170° C.

The resulting zeolites are isolated in a customary manner, for example by filtration, and are washed and dried.

In the process according to the invention, the zeolites are preferably employed in their acid form. These acid forms can be prepared by complete or partial ion exchange, by known methods, from the alkali metal forms, such as are generally obtained in the zeolite synthesis or occur as natural products. A customary method for the preparation of the H-form of a zeolite consists, for example, in first converting the alkali metal form into the ammonium form by partial or complete ion exchange with an ammonium salt solution, and then converting this form into the H-form by calcination. However, the forms in which exchange has been carried out with alkali, alkaline earth or rare earth metal ions also display catalytic activity.

The zeolite catalysts according to the invention are composed, in general, of the catalytically active zeolite component and a binder material. The latter is required in order to convert the zeolite into an external shape suitable for the process according to the invention.

Suitable binder materials are, above all, oxides or hydroxides of aluminum and the oxides or hydroxides of silicon and also phyllosilicates, for example those of the kaolin or montmorillonite family.

This zeolite catalyst, prepared in this way, is usually first activated by calcination at temperatures between 300° and 700° C. before being employed in the isomerization reaction according to the invention. In order to impart better stability to the catalyst, it is sometimes advantageous to carry out the calcination in the presence of steam, ammonia or mixtures thereof.

If the reaction is carried out in the gas phase, an advantageous, simple procedure for carrying out the isomerization according to the invention consists in passing the monochlorotoluenes or dichlorotoluenes - in the case of the latter, if appropriate also the diluent - from a metering device first into a vaporization zone and then passing the resulting gas through an externally heated reaction tube filled with the catalyst. If the isomerization is carried out in the liquid phase, the feed material is first warmed and is then passed in liquid form through the reaction tube filled with the catalyst.

In respect of the service life of the catalyst, it has proved advantageous also to mix hydrogen or steam into the feed material.

In addition, it can also be advantageous to mix in a carrier gas which is inert under the reaction conditions. Examples of suitable carrier gases are nitrogen and noble gases.

Hydrogen, steam and/or the carrier gas are added in such an amount that the dwell time is between one and a hundred seconds.

The mixing of the hydrogen, steam and/or carrier gas with the monochlorotoluene(s) or the dichlorotoluene(s) is effected most advantageously in the vaporization or heating zone. It has proved advantageous in this respect to heat these gases to reaction temperature before mixing.

The isomerization according to the invention is generally carried out at temperatures between 200° and 550° C., preferably at 250° to 500° C., and under pressures of 0.1 to 30 bar, preferably 1 to 20 bar and especially at normal pressure. The loading of the zeolite catalyst, expressed at LHSV (Liquid Hourly Space Velocity, hours$^{-1}$), is generally between 0.05 and 10 hours$^{-1}$, preferably between 0.2 and 5 hours$^{-1}$.

After leaving the reactor, the reaction products are cooled in order to remove the condensable components. The isomerization according to the invention is, however, not limited to this procedure (fixed bed reactor), but can, in principle, also be carried out in other suitable types of reactors (for example a fluidized bed reactor).

The unreacted starting material can be recycled to the reactor after separation by distillation, crystallization or selective adsorption.

If the activity of the catalyst should decrease in the course of time as a result of coking, it can be regenerated. This is effected by passing oxygen, air, nitrogen/air, oxygen/air, oxygen/inert gas or air/inert gas over the deactivated catalyst at temperatures between 300° and 650° C. Nitrogen/air is preferred in this respect. The temperature in this process should not exceed 650° C. at any point in the reactor. After regeneration, the catalyst once more has its full activity.

Monochlorotoluenes and dichlorotoluenes are important intermediate products for the preparation of dyestuffs, pharmaceuticals, preservatives and plant protection agents and are also used as starting materials for the preparation of a number of chlorine-containing aromatic compounds.

The invention will be illustrated by means of the examples which follow, but the examples are not intended in any way to be limiting.

EXAMPLES

Example 1 (Isomerization of 2-chlorotoluene on a zirconium-containing zeolite of the Pentasil type)

(a) Preparation of the catalyst

A zirconoaluminosilicate of the Pentasil type was prepared in accordance with Example 1 of European Patent No. A2-77,523, as follows: 16.6 g of sodium aluminate (54% by weight of $Al_2O_3$ and 41% by weight of $Na_2O$) and 14.8 g of sodium hydroxide were dissolved in 200 g of 20% strength by weight aqueous tetrapropylammonium hydroxide solution (solution A). A further solution (solution B) was prepared by dissolving 620 g of 40% strength by weight colloidal silica gel in 2,300 g of 20% strength by weight aqueous tetrapropylammonium hydroxide solution, and concentrating this solution to a total of 2,200 g on a rotary evaporator. Solution A and solution B were mixed with one another. 37.8 g of zirconyl chloride $ZrOCl_2.8 H_2O$ were added to this mixture with vigorous stirring. The resulting suspension was homogenized and heated at 160° C. for 120 hours in a closed vessel. The resulting product was filtered off, washed with water and dried at 120° C. 273 g of zirconoaluminosilicate were obtained. X-ray defraction analysis indicated a well-crystalline product having a ZSM-5 structure.

The powder was then calcined in air for 2 hours at 400° C., 3 hours at 450° C. and 8 hours at 500° C.

Expressed in molar ratios of the oxides, this material had the following composition:

$SiO_2$: 0.035 $ZrO_2$: 0.026 $Al_2O_3$: 0.023 $Na_2O$.

It was treated three times with 1-molar ammonium nitrate solution for several hours at 100° C. and was washed, dried and calcined in air for several hours at 500° C.

65 g of the powder thus obtained were processed together with 35 g of $Al_2O_3$ to give extrudates of diameter 1.6 mm, which were calcined for 4 hours at 500° C., comminuted to a particle size of 0.25 to 1.0 mm and calcined at 450° C. in a stream of hydrogen for 2 hours.

(b) Isomerization 15 ml of the catalyst prepared in accordance with (a) were introduced into a tubular glass reactor of internal diameter 16 mm and length 56 cm and were covered with a layer of glass spheres in order to vaporize the liquid starting material. It was possible to measure the temperature in the catalyst bed by means of a thermocouple which was located in the center of the reactor and which could be moved in an axial direction. The reactor and the vaporization zone were located in an electrically heated oven. 6 ml/hour of 2-chlorotoluene were fed into the reactor via a metering pump. 10 l/hour of hydrogen were also passed over the catalyst via a gas supply comprising reducing valves and devices for measuring the pressure and flow rate. The condensable reaction products were condensed in a cold trap at 0° C. and were weighed and analyzed by gas chromatography.

The results are shown in Table 1:

TABLE 1

Isomerization of 2-chlorotoluene on zirconium-containing Pentasil

| Duration of test (hours) | Temperature (°C.) | Conversion of 2-chlorotoluene (%) | Selectivity of conversion to: | | |
|---|---|---|---|---|---|
| | | | 3-chlorotoluene (%) | 4-chlorotoluene (%) | toluene (%) |
| 1–20 | 250–340 | 15.3* | 82.2* | 12.1* | 5.1* |
| 21 | 370 | 20.3 | 76.1 | 17.0 | 5.3 |
| 46 | 370 | 11.6 | 75.3 | 17.3 | 5.9 |
| 47 | 400 | 35.4 | 68.3 | 21.3 | 5.8 |
| 66 | 400 | 23.5 | 69.4 | 22.9 | 5.8 |
| 89 | 400 | 17.3 | 70.2 | 22.4 | 5.5 |
| 90 | 430 | 42.0 | 64.4 | 21.8 | 8.0 |
| 122 | 430 | 26.9 | 66.3 | 24.3 | 7.0 |
| 148 | 430 | 27.4 | 66.5 | 24.7 | 7.0 |
| 164 | 430 | 27.8 | 67.2 | 25.7 | 5.9 |
| 179 | 430 | 27.0 | 67.0 | 26.2 | 5.6 |
| 194 | 430 | 26.3 | 67.8 | 25.8 | 5.2 |
| 210 | 430 | 24.5 | 66.9 | 26.3 | 5.0 |

*Average value over 20 hours

As can be seen from the table, although the catalyst initially exhibited deactivation after every increase in temperature, a constant activity and selectivity of conversion were observed from the 122nd hour up to the end of the experiment after 210 hours. The selectivity of the formation of toluene averages about 6%.

The selectivity of the formation of X is understood to mean the proportion of the reacted feed product which reacts to form X.

Comparison Example 1 (Isomerization of 2-chlorotoluene on H-ZSM-5)

This isomerization was carried out under the same conditions as in Example 1, but using as catalyst 15 ml of H-ZSM-5, the preparation of which is described, for example, in U.S. Pat. No. 3,702,886.

TABLE 2

| | Isomerization of 2-chlorotoluene on H-ZSM-5 | | | | |
|---|---|---|---|---|---|
| Duration of test (hours) | Temperature (°C.) | Conversion of 2-chlorotoluene (%) | Selectivity of conversion to: | | |
| | | | 3-chloro-toluene (%) | 4-chloro-toluene (%) | toluene (%) |
| 1–16 | 250–370 | 22.4* | 65.3* | 26.0* | 5.2* |
| 17 | 400 | 31.3 | 60.9 | 27.3 | 8.8 |
| 23 | 400 | 16.6 | 55.7 | 34.5 | 8.3 |
| 24 | 430 | 28.6 | 56.6 | 27.2 | 13.0 |
| 30 | 430 | 19.2 | 56.2 | 29.9 | 12.0 |

*Average value over 16 hours

A comparison with Example 1 shows that, although H-ZSM-5 has an activity comparable with the zirconium-containing Pentasil at the start of the experiment, its conversion decreases appreciably more rapidly at temperatures as low as 400° C., and, at 430° C., it displays both a lower initial conversion and a rapid decline of the conversion considerably below the constant level reached in Example 1. In addition, the selectivity of the formation of the by-product toluene is lower on the Pentasil according to the invention.

Example 2 (Isomerization of 2,4-dichlorotoluene on zirconium-containing Pentasil)

(a) Preparation of the catalyst

A zirconoaluminosilicate of the Pentasil type was prepared as described in part a) of Example 1.

(b) Isomerization

The procedure was as in part b) of Example 1, except that 6 ml/hour of 2,4-dichlorotoluene instead of 2-chlorotoluene were now fed into the reactor.

The results are shown in Table 3:

TABLE 3

| | | Contents of the product in % by weight | | | | | | | | |
|---|---|---|---|---|---|---|---|---|---|---|
| Duration (hours) | Temperature (°C.) | 2,4-DCT | 2,5-DCT | 3,4-DCT | 2,3-DCT | 3,5-DCT | CT | o-DCB | m-DCB | p-DCB |
| 4 | 400 | 59.4 | 25.8 | 7.0 | <0.1 | <0.1 | 1.4 | <0.1 | 6.9 | <0.1 |
| 6 | 400 | 62.8 | 23.9 | 5.2 | <0.1 | <0.1 | 1.3 | <0.1 | 5.2 | <0.1 |
| 8 | 400 | 64.5 | 23.1 | 6.0 | <0.1 | <0.1 | 1.1 | <0.1 | 4.9 | <0.1 |
| 10 | 400 | 67.7 | 20.9 | 5.6 | <0.1 | <0.1 | 0.9 | <0.1 | 4.6 | <0.1 |
| 12 | 400 | 69.4 | 19.9 | 5.2 | <0.1 | <0.1 | 0.9 | <0.1 | 4.3 | <0.1 |
| 14 | 400 | 68.9 | 20.5 | 5.3 | <0.1 | <0.1 | 0.8 | <0.1 | 4.2 | <0.1 |
| 20 | 400 | 73.4 | 17.6 | 4.6 | <0.1 | <0.1 | 0.6 | <0.1 | 3.5 | <0.1 |

Isomerization of 2,4-dichlorotoluene on zirconium-containing Pentasil
DCT: dichlorotoluene
CT: chlorotoluene
DCB: dichlorobenzene Comparison Example 2 (Isomerization of 2,4-dichlorotoluene on H-ZSM-5)

This isomerization was carried out under the same conditions as in Example 2, but using as catalyst 15 ml of H-ZSM-5, the preparation of which is described in U.S. Pat. No. 3,702,886, Example 1.

The results are shown in Table 4.

A comparison with Example 2 shows that, although H-ZSM-5 has an activity comparable with the zirconium-containing Pentasil at the start of the experiment, the conversion of 2,4-dichlorotoluene and the yield of 2,5-dichlorotoluene and 3,4-dichlorotoluene decrease much more rapidly than when the zirconium-containing zeolite of the Pentasil type, accoroing to the invention, is employed.

TABLE 4

| | | Contents of the product in % by weight | | | | | | | | |
|---|---|---|---|---|---|---|---|---|---|---|
| Duration (hours) | Temperature (°C.) | 2,4-DCT | 2,5-DCT | 3,4-DCT | 2,3-DCT | 3,5-DCT | CT | o-DCB | m-DCB | p-DCB |
| 1 | 400 | 36.9 | 29.9 | 8.9 | <0.1 | <0.1 | 7.4 | <0.1 | 7.0 | 5.3 |
| 2 | 400 | 48.1 | 28.3 | 6.8 | <0.1 | <0.1 | 5.1 | <0.1 | 5.9 | 3.7 |
| 4 | 400 | 61.9 | 22.0 | 5.7 | <0.1 | <0.1 | 2.8 | <0.1 | 4.2 | 2.3 |
| 6 | 400 | 69.7 | 18.0 | 4.9 | <0.1 | <0.1 | 1.7 | <0.1 | 3.2 | 1.6 |
| 8 | 400 | 74.5 | 15.4 | 4.4 | <0.1 | <0.1 | 1.2 | <0.1 | 2.5 | 1.3 |
| 10 | 400 | 77.5 | 13.6 | 4.0 | <0.1 | <0.1 | 0.6 | <0.1 | 2.1 | 1.0 |
| 12 | 400 | 80.6 | 11.9 | 3.6 | <0.1 | <0.1 | 0.6 | <0.1 | 1.9 | 0.9 |
| 14 | 400 | 80.4 | 12.1 | 3.7 | <0.1 | <0.1 | 0.5 | <0.1 | 1.8 | 0.9 |
| 20 | 400 | 91.2 | 5.6 | 1.7 | <0.1 | <0.1 | 0.1 | <0.1 | 0.7 | 0.3 |

Isomerization of 2,4-dichlorotoluene on H-ZSM-5
DCT: dichlorotoluene
CT: chlorotoluene
DCB: dichlorobenzene Example 3 (Isomerization of 3,4-dichlorotoluene on regenerated zirconium-containing Pentasil)

The catalyst already used in Example 2 was regenerated for 2 hours at 600° C. in an atmosphere of air.

The test described in Example 2 was then carried out with this catalyst using 3,4-dichlorotoluene as the feed material instead of 2,4-dichlorotoluene. Table 5 shows that 3,4-dichlorotoluene can also be isomerized on a zirconium-containing zeolite of the Pentasil type.

chlorotoluene on a zeolite catalyst, which comprises using a zirconoaluinosilicate of the Pentasil type.

TABLE 5

| Duration (hours) | Temperature (°C.) | Contents of the product in % by weight | | | | | | | |
|---|---|---|---|---|---|---|---|---|---|
| | | 3,4-DCT | 2,5-DCT | 2,4-DCT | 2,3-DCT | 3,5-DCT | CT | o-DCB | m-DCB | p-DCB |
| 1 | 400 | 29.7 | 26.7 | 23.0 | <0.1 | <0.1 | 3.5 | <0.1 | 8.3 | 4.6 |
| 2 | 400 | 37.8 | 22.9 | 18.6 | <0.1 | <0.1 | 2.9 | <0.1 | 9.9 | 5.1 |
| 4 | 400 | 57.8 | 12.6 | 9.9 | <0.1 | <0.1 | 2.2 | <0.1 | 10.7 | 4.2 |
| 6 | 400 | 67.3 | 8.8 | 6.5 | <0.1 | <0.1 | 1.6 | <0.1 | 10.5 | 3.2 |
| 8 | 400 | 72.3 | 6.8 | 5.2 | <0.1 | <0.1 | 1.3 | <0.1 | 10.1 | 2.6 |
| 10 | 400 | 79.2 | 4.7 | 3.5 | <0.1 | <0.1 | 0.9 | <0.1 | 8.8 | 1.8 |
| 12 | 400 | 85.6 | 3.0 | 2.1 | <0.1 | <0.1 | 0.6 | <0.1 | 6.7 | 1.1 |

Isomerization of 3,4-dichlorotoluene on regenerated zirconium-containing Pentasil
DCT: dichlorotoluene
CT: chlorotoluene
DCB: dichlorobenzene Example 4 (Isomerization of 2,4-dichlorotoluene on regenerated zirconium-containing Pentasil)

The catalyst already used in Example 2 and 3 was regenerated for 2 hours at 600° C. in an atmosphere of air. The test described in Example 2 was then repeated with this catalyst. As Table 6 shows, after regeneration, the catalyst according to the invention has the same activity and gives the same distribution of products as a fresh catalyst.

TABLE 6

| Duration (hours) | Temperature (°C.) | Contents of the product in % by weight | | | | | | | |
|---|---|---|---|---|---|---|---|---|---|
| | | 2,4-DCT | 2,5-DCT | 3,4-DCT | 2,3-DCT | 3,5-DCT | CT | o-DCB | m-DCB | p-DCB |
| 1 | 400 | 53.0 | 31.1 | 8.2 | <0.1 | <0.1 | 1.9 | <0.1 | <0.1 | 0.2 |
| 2 | 400 | 57.0 | 28.8 | 7.8 | <0.1 | <0.1 | 1.5 | <0.1 | <0.1 | 0.2 |
| 4 | 400 | 62.7 | 25.3 | 6.9 | <0.1 | <0.1 | 1.3 | <0.1 | <0.1 | <0.1 |
| 6 | 400 | 66.3 | 23.1 | 6.4 | <0.1 | <0.1 | 1.0 | <0.1 | <0.1 | <0.1 |
| 8 | 400 | 69.1 | 21.2 | 6.0 | <0.1 | <0.1 | 2.8 | <0.1 | <0.1 | <0.1 |
| 10 | 400 | 68.0 | 22.2 | 5.5 | <0.1 | <0.1 | 3.3 | <0.1 | <0.1 | <0.1 |
| 12 | 400 | 72.6 | 18.9 | 5.4 | <0.1 | <0.1 | 2.3 | <0.1 | <0.1 | <0.1 |
| 14 | 400 | 72.5 | 19.0 | 5.6 | <0.1 | <0.1 | 2.3 | <0.1 | <0.1 | <0.1 |
| 16 | 400 | 72.7 | 18.9 | 5.6 | <0.1 | <0.1 | 2.2 | <0.1 | <0.1 | <0.1 |

Isomerization of 2,4-dichlorotoluene on regenerated zirconium-containing Pentasil
DCT: dichlorotoluene
CT: chlorotoluene
DCB: dichlorobenzene

We claim:

1. A process for isomerizing one or more monochlorotoluenes or one or more dichlorotoluenes on a zeolite catalyst, which comprises using a zirconoaluminosilicate zeolite of the Pentasil type.

2. A process for isomerizing one or more monochlorotoluenes on a zeolite catalyst, which comprises using a zirconoaluminosilicate of the Pentasil type.

3. A process for the preparation of a mixture of 3-chlorotoluene and 4-chlorotoluene by isomerizing 2-chlorotoluene on a zeolite catalyst, which comprises using a zirconoaluinosilicate of the Pentasil type.

4. A process for isomerizing one or more dichlorotoluenes on a zeolite catalyst, which comprises using a zirconoaluminosilicate of the Pentasil type.

5. A process for isomerizing 2,4-dichlorotoluene on a zeolite catalyst, which comprises using a zirconoaluminosilicate of the Pentasil type.

6. A process for isomerizing 3,4-dichlorotoluene on a zeolite catalyst, which comprises using a zirconoaluminosilicate of the Pentasil type.

7. The process as claimed in claim 1 wherein the zirconoaluminosilicate of the Pentasil type contains protons as cations.

8. The process as claimed in claim 1 wherein the reaction is carried out at a temperature between 200° and 550° C.

9. The process as claimed in claim 1 wherein the reaction is carried out at a pressure between 0.1 bar and 30 bar.

10. The process as claimed in claim 1 wherein the isomerization is carried out in the presence of hydrogen, nitrogen, steam, argon or a mixture thereof.

* * * * *